(12) United States Patent
Bene

(10) Patent No.: US 7,351,218 B2
(45) Date of Patent: Apr. 1, 2008

(54) DEVICE AND PROCESS FOR EXTRACORPOREAL TREATMENT BY CITRATE ANTICOAGULANT

(75) Inventor: Bernard Bene, Irigny (FR)

(73) Assignee: Gambro Lundia AB, Lund (SE)

( * ) Notice: Subject to any disclaimer, the term of this patent is extended or adjusted under 35 U.S.C. 154(b) by 374 days.

(21) Appl. No.: 10/739,273

(22) Filed: Dec. 19, 2003

(65) Prior Publication Data

US 2004/0133145 A1 Jul. 8, 2004

Related U.S. Application Data

(60) Provisional application No. 60/453,967, filed on Mar. 13, 2003.

(30) Foreign Application Priority Data

Dec. 20, 2002 (FR) .................................. 02 16228

(51) Int. Cl.
*A61M 37/00* (2006.01)
(52) U.S. Cl. .................... 604/6.07; 604/5.01; 604/6.06; 210/739
(58) Field of Classification Search .............. 604/6.07, 604/5.01, 5.04, 6.06; 210/739; 422/47
See application file for complete search history.

(56) References Cited

U.S. PATENT DOCUMENTS

| | | | |
|---|---|---|---|
| 3,946,731 A * | 3/1976 | Lichtenstein ................. | 604/66 |
| 4,464,164 A * | 8/1984 | Troutner et al. ........... | 604/6.05 |
| 4,490,135 A | 12/1984 | Troutner | |
| 4,500,309 A | 2/1985 | Diederich et al. | |
| 4,571,244 A * | 2/1986 | Knighton ..................... | 604/118 |
| 4,894,150 A * | 1/1990 | Schurek et al. ............. | 210/101 |
| 5,032,615 A * | 7/1991 | Ward et al. ................. | 514/574 |
| 5,205,153 A * | 4/1993 | Hlavinka et al. .......... | 73/19.03 |
| 5,330,425 A | 7/1994 | Utterberg | |
| 5,344,568 A | 9/1994 | Kitaevich et al. | |

(Continued)

FOREIGN PATENT DOCUMENTS

EP 0 317 766 B1 5/1989

(Continued)

OTHER PUBLICATIONS

Entries on sodium citrate and citric acid, pp. 274 and 1013, Hawley's Condensed Chemical Dictionary, 13th Ed. 1997.*

*Primary Examiner*—Tatyana Zalukaeva
*Assistant Examiner*—Paula L. Craig
(74) *Attorney, Agent, or Firm*—Finnegan, Henderson, Farabow, Garrett & Dunner, L.L.P.

(57) ABSTRACT

A device for treating blood by extracorporeal circulation comprising a filter having a first chamber and a second chamber separated by a semi-permeable membrane. The device has an arterial line connected to the first chamber of the filter, a venous line issuing from the first chamber of the filter, a channel used for pre-infusion of a substance for regional anticoagulation and linked to the arterial line, a purge channel issuing from the second chamber of the filter, and an air separator on the venous line. The device also includes a line for post-infusion of a solution at least partially re-establishing the ionic equilibrium of the blood downstream of the air separator, the post-infusion line being configured immediately upstream of an air detector.

25 Claims, 3 Drawing Sheets

U.S. PATENT DOCUMENTS

| | | | |
|---|---|---|---|
| 5,470,483 A * | 11/1995 | Bene et al. | 210/741 |
| 5,529,685 A * | 6/1996 | Irie et al. | 210/134 |
| 5,578,223 A * | 11/1996 | Bene et al. | 210/85 |
| 5,650,071 A * | 7/1997 | Brugger et al. | 210/646 |
| 5,676,841 A * | 10/1997 | Brown | 210/739 |
| 5,762,805 A * | 6/1998 | Truitt et al. | 210/645 |
| 6,123,847 A * | 9/2000 | Bene | 210/646 |
| 6,454,736 B1 * | 9/2002 | Ludt et al. | 604/5.01 |
| 6,561,997 B1 * | 5/2003 | Weitzel et al. | 604/6.09 |
| 6,572,576 B2 * | 6/2003 | Brugger et al. | 604/4.01 |
| 6,726,647 B1 * | 4/2004 | Sternby et al. | 604/6.09 |
| 6,743,191 B1 * | 6/2004 | Chang | 604/4.01 |
| 7,029,456 B2 * | 4/2006 | Ware et al. | 604/131 |
| 2002/0004530 A1 * | 1/2002 | Warnock | 514/574 |
| 2003/0045827 A1 * | 3/2003 | Nier et al. | 604/5.01 |

FOREIGN PATENT DOCUMENTS

| | | |
|---|---|---|
| EP | 0 578 175 A1 | 1/1994 |
| EP | 0 587 101 B1 | 3/1994 |
| EP | 0 829 265 A1 | 3/1998 |
| WO | WO 00/64456 | 11/2000 |

* cited by examiner

DEVICE AND PROCESS FOR EXTRACORPOREAL TREATMENT BY CITRATE ANTICOAGULANT

CROSS REFERENCE TO RELATED APPLICATIONS

This application claims the priority of French patent application No. 02 16228, filed on Dec. 20, 2002, and the benefit of U.S. Provisional Application No. 60/453,967, filed on Mar. 13, 2003, the contents of which are incorporated herein by reference.

BACKGROUND OF THE INVENTION

The present invention relates to a device for treating blood by extracorporeal circulation, a disposable line for use in a circuit for extracorporeal circulation of blood having undergone pre-infusion of anticoagulant, and a method for anticoagulation of the blood treated by extracorporeal circulation.

A haemodialysis session requires anticoagulation of the blood circulating in the extracorporeal circulation line in order to avoid coagulation of the blood in contact with the synthetic materials (circulation lines, dialyser fibres). This anticoagulation is most often performed using heparin, which is known for its anticoagulant properties. Heparin is injected as pre-infusion into the arterial line of the device, and it is then present in the entire extracorporeal circuit of the blood, from pre-infusion until re-injection of the blood into the patient. Consequently, upon return of the blood, the patient is administered doses of heparin. Although it is necessary to prevent coagulation in the extracorporeal circulation line, in some cases the risk of the patient bleeding may pose a danger. This is particularly true of patients at high risk of haemorrhaging (for example in the days following major surgery) or in those patients with hypersensitivity to heparin. Consequently, anti-coagulation with heparin may prove dangerous to the patient on account of heparin being injected via the return of blood to the patient.

FIG. 1 shows a device for treating blood by extracorporeal circulation 1 according to the prior art, comprising a filter 2 having a first chamber 3 and a second chamber 4 separated by a semi-permeable membrane 5. The device comprises an arterial line 6 connected to the first chamber 3 of the filter for the circulation of blood taken from a patient 7, and a venous line 8 issuing from the first chamber of the filter. A pre-infusion channel 9 is connected to a container 10 comprising a solution of heparin and is linked to the arterial line 6, the function of the solution being to prevent coagulation of the blood outside the patient's body, and a purge channel 11 issuing from the second chamber 4 of the filter. An air separator 12 is linked to the venous line 8. The air separator 12 also comprises an air detector 13, and a clamp 14 is placed on the venous line 8 downstream of the air separator 12, that is to say downstream in the direction of circulation of the blood in the venous line 8. The clamp allows the flow of blood to be arrested in the event of air bubbles being detected by the detector 13 before the blood returns to the patient 7.

Thus, as was mentioned above, the solution of heparin acts against coagulation of the blood throughout the device 1 and also in the patient's body. Consequently, the return and injection of heparin into the body of the patient 7 can prove dangerous.

Patent application PCT/EP00/03583 concerns an infusion fluid of substitution, in particular for use in haemofiltration of blood, and an anticoagulant solution with citrate for regional anticoagulation. In order to avoid coagulation of blood during a haemodialysis session, it is known that citrate ions can be used as anticoagulant. The citrate ions, added to the blood in the extracorporeal circuit before they enter the artificial kidney, are active as anticoagulants. Thus, the risk of complications with bleeding due to systematic anticoagulation is avoided. During the haemofiltration, some of the citrate ions pass through the artificial kidney. The citrate ions are active as anticoagulants only in the extracorporeal circuit because, when they reach the systemic circulation of the patient, they are rapidly metabolized to bicarbonate ions. The subject of patent application PCT/EP00/03583 is a solution of a certain composition.

FIG. 2 shows a device for treating blood by extracorporeal circulation 1 described in patent application PCT/EP00/03583. This device 1 comprises a filter 2 having a first chamber 3 and a second chamber 4 separated by a semi-permeable membrane 5. The device comprises an arterial line 6 connected to the first chamber 3 of the filter for the circulation of blood taken from a patient 7, and a venous line 8 issuing from the first chamber of the filter. A pre-infusion channel 9 containing an anticoagulant, trisodium citrate, is connected to a container 10 comprising a solution of citrate ions and is linked to the arterial line 6, the function of the solution being to prevent coagulation of the blood outside the patient's body. A purge channel 11 is linked to the outlet of the second chamber 4 of the filter, and an air separator 12 is linked on the venous line 8.

The venous line 8 comprises, in addition to the bubble trap 12, a channel 13 connected to a container 14 comprising a solution for re-establishing the ionic equilibrium of the blood. The citrate solution renders the blood anticoagulable by decalcifying it upstream of the filter. This channel 13 is linked downstream of the bubble trap 12, that is to say downstream in the direction of circulation of the blood in the venous line 8 before the blood is returned to the patient 7.

The reason is that, in order to re-establish correct haemostasis, the ionic equilibrium of the blood must be re-established, specifically by recalcifying it, after leaving the filter.

The teaching of this document comprises a safety device with which it is possible to detect any air bubbles present at the start of the venous line. By contrast, the device described does not have any safety means for detecting and trapping any air bubbles in the post-infusion line linked to the venous line, and return of air to the systemic circulation of the patient, which is very dangerous for said patient, is possible.

In seeking to solve this problem, the persons skilled in the art have tried linking the post-infusion line, containing an infusion solution of substitution, directly to the bubble trap of the venous line and not downstream thereof. Moreover, the bubble detector has been placed on this bubble trap. In this way, a single device makes it possible simultaneously to separate and detect the air bubbles coming from, on the one hand, the blood liquid extracted from the filter and, on the other hand, coming from the post-infusion liquid.

However, in trials carried out with this set-up, it has been found, especially in prolonged operation, for example with slow blood flowrates in an intensive care unit, that although the problem of air bubbles in the two liquids is solved, a new problem arises: namely that of coagulation within the bubble trap. This is because the blood liquid extracted from the filter and arriving in the bubble trap comprises an anticoagulant liquid which has been injected in pre-infusion into the patient's blood during its passage through the arterial line. Moreover, the bubble trap also receives an infusion solution of substitution, whose effect is to neutralize the anticoagulant effect of the pre-infusion solution. The structure of the bubble trap is such that on the one hand the liquid passing inside the latter is in contact with the air and the risk of coagulation is present, and, on the other hand, as the bubble trap has a greater diameter than the diameter of the venous line, the flowrate of liquid is thereby diminished and the phenomenon of coagulation thereby promoted.

It is also known in U.S. Pat. No. 5,330,425 (Utterberg) a device concerning the injection in the venous line of drugs and the like. It is also known an haemodialysis machine having an air-detector/line clamp assembly mounted on the venous line typically at least two inches below a venous chamber, in which it is possible to design a venous bloodline wherein an injection site is placed in the tubing downstream of the venous chamber, yet upstream of the air-detector/line clamp.

BRIEF SUMMARY OF THE INVENTION

Another prior art is the patent U.S. Pat. No. 4,490,135 (Troutner) which discloses a single needle haemodialysis system having two air detectors on the venous line.

There is therefore the twin problem of detecting the bubbles in each of the two liquids using a device of simple structure, and of preventing coagulation of the blood throughout the extracorporeal circuit.

The object of the present invention is to make available a device with which it is possible to solve this problem.

To achieve this object, the invention provides a device for treating blood by extracorporeal circulation (101) comprising:
  a filter (102) having a first chamber (103) and a second chamber (104) separated by a semi-permeable membrane (105),
  an arterial line (106) connected to the first chamber (103) of the filter (102),
  a venous line (108) issuing from the first chamber (103) of the filter (102),
  a channel (109) used for pre-infusion of a substance for regional anticoagulation and linked to the arterial line (106),
  a purge channel (110) issuing from the second chamber (104) of the filter (102),
  an air separator (111) on the venous line (108),
  a line (112) for post-infusion of a solution at least partially re-establishing the ionic equilibrium of the blood downstream of the air separator (111),
  an air detector (113) downstream of the post-infusion line (112).

The invention also relates to a disposable venous line (108) for use in a circuit for extracorporeal circulation of blood having undergone pre-infusion of anticoagulant, comprising:
  a first channel (134) having a first connector (135) for linking to a filter and a second connector (136),
  an air separator (111) linked to the second connector (136) downstream of the first channel (134),
  a second channel (137) having a third connector (138) for linking to the outlet of the air separator (111) and a fourth connector (139) for linking to the blood access of a patient,
  a fifth connector (140) for linking a line (112) for post-infusion of a solution at least partially re-establishing the ionic equilibrium of the blood, the fifth connector permitting fluid communication with the second channel (137),
  a first part (141) of the second channel (137) connectable to an air detector (113) and placed downstream of the fifth connector (140).

The invention also concerns a device for treating blood by extracorporeal circulation comprising said disposable venous line and according to the alternative embodiments of the disposable venous line.

Finally, the invention relates to a method of treating blood, comprising the following steps:
  infusing a substance for regional anti-coagulation into what is called an arterial line carrying blood which has been taken beforehand from a patient,
  passing the extracted blood through a filter,
  after passage of the blood through the filter, eliminating the possible presence of air in the blood circulating in what is called a venous line,
  after possible elimination of the air, infusing a solution at least partially re-establishing the ionic equilibrium of the blood,
  after infusion of solution to re-establish the ionic equilibrium, detecting the possible presence of air,
  in the event of air being detected, clamping what is called the venous line downstream of the post-infusion, without passing through a second air separator placed downstream of the first air separator.

The invention also concerns a method of extracorporeal blood treatment, comprising the following steps:
  extracting blood from a patient at a given flowrate,
  infusing a substance for regional anti-coagulation into the extracted blood,
  passing the extracted blood through a filter,
  after passage of the blood through the filter, eliminating the possible presence of air in the blood passing through a venous line,
  after possible elimination of air, infusing a solution at least partially re-establishing the ionic equilibrium of the blood,
  after infusion of solution to re-establish the ionic equilibrium, detecting the possible presence of air,
  in the event of air being detected, clamping the venous line downstream of the post-infusion,
  returning the blood to the patient, without passing through a second air separator placed downstream of the first air separator.

Other advantages and characteristics of the invention will become evident from reading the description which follows.

BRIEF DESCRIPTION OF THE SEVERAL VIEWS OF THE DRAWINGS

Reference will be made to the attached drawings, in which.

DETAILED DESCRIPTION OF THE INVENTION

Figure 1:
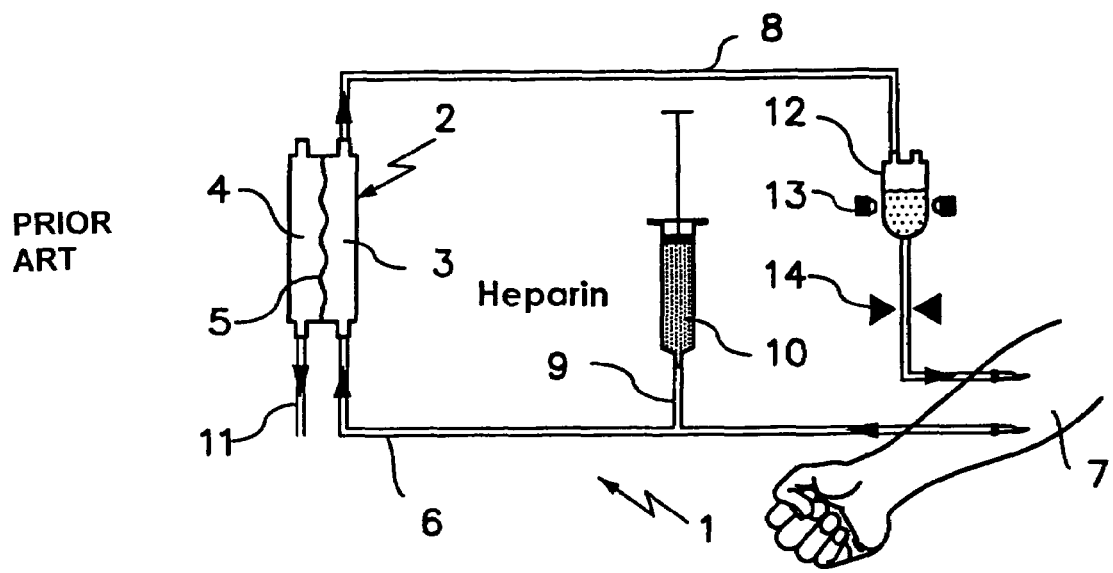
FIG. 1 shows the prior art in terms of an apparatus for extracorporeal treatment of blood with prevention of anticoagulation by heparin.
Figure 2:
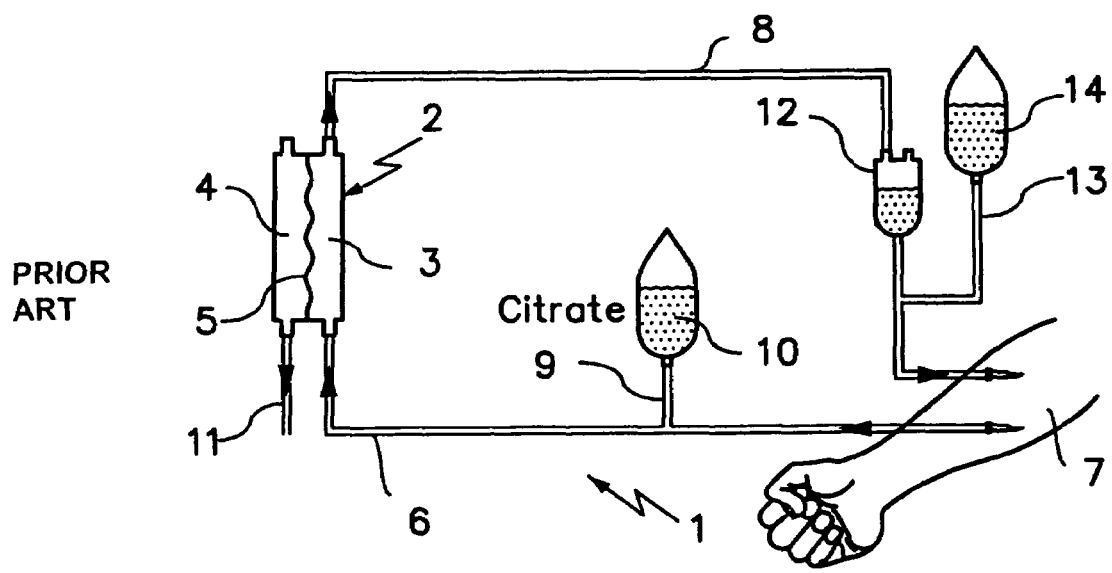
FIG. 2 shows the prior art in terms of an apparatus for extracorporeal treatment of blood with prevention of anticoagulation by citrate.
Figure 3:
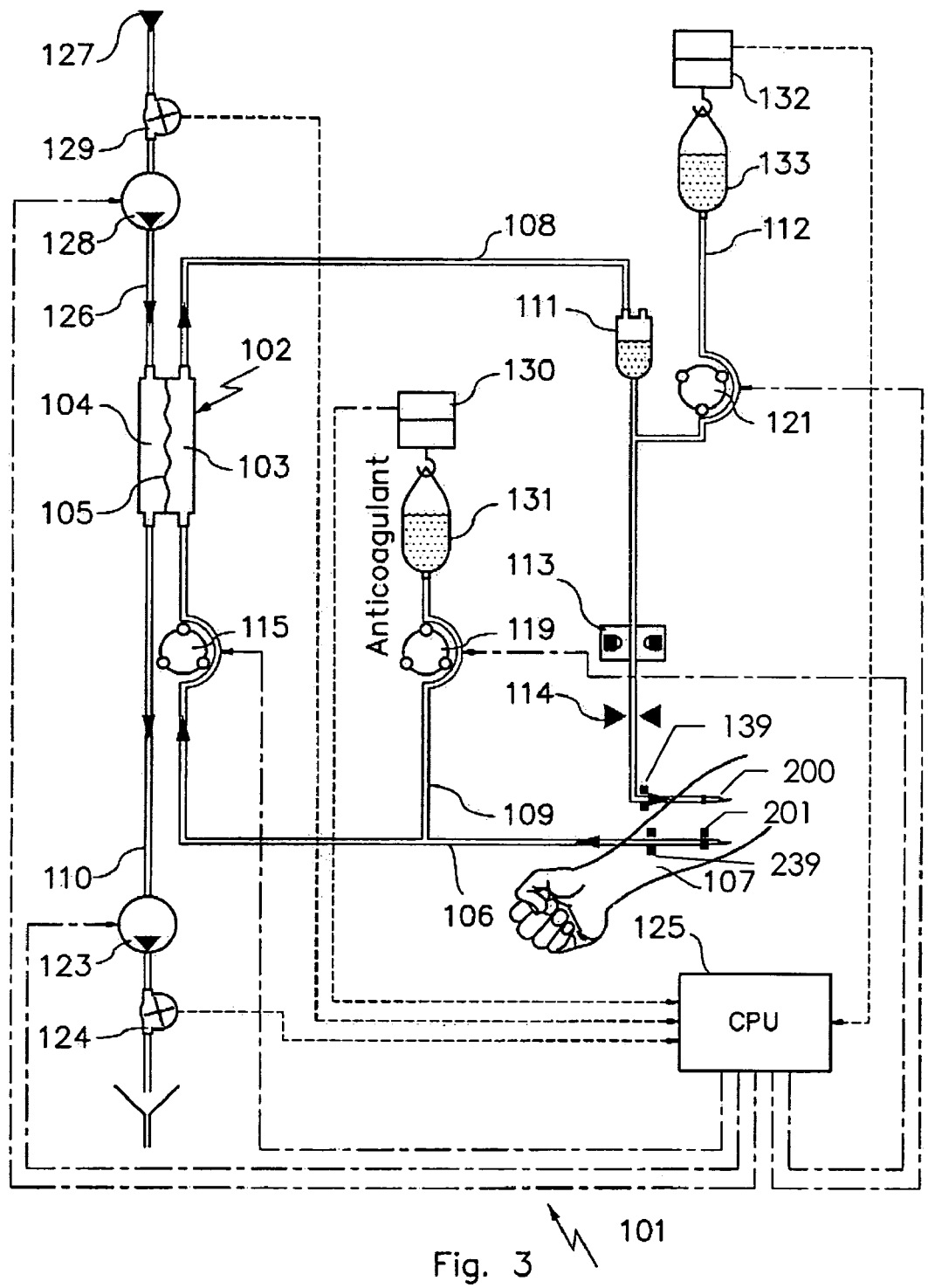
FIG. 3 shows the device for treating blood by extracorporeal circulation according to the invention.

FIG. 3 shows the device for extracorporeal treatment of blood according to the invention, set up to carry out dialysis treatment. The device for treating blood by extracorporeal circulation 101 according to the invention comprises a filter 102 having a first chamber 103 and a second chamber 104 separated by a semipermeable membrane 105. Depending on the membrane, the filter 105 can be a haemofilter, a plasma filter, a dialyser, or a filter of another type. As regards the membrane, the membranes used are hollow-fibre membranes or sheet or tube membranes. An arterial line 106 is connected to the first chamber 103 of the filter for circulation of blood taken from a patient 107. A venous line 108 is connected to the outlet of the first chamber 103 of the filter. A channel 109 for pre-infusion of a substance for regional anticoagulation is linked to the arterial line 106. A purge channel 110 is connected to the outlet of the second chamber 104 of the filter. An air separator 111 is placed on the venous line 108 and a post-infusion line 112 for a solution at least partially re-establishing the ionic equilibrium is placed downstream of the air separator 111, that is to say downstream in the direction of circulation of the blood in the venous line 108. Finally, an air detector 113 is placed downstream of the post-infusion line 112.

No other air separator is inserted downstream of the air detector 113. The air separator 111 can also be the only air separator present in the venous line 108 and does not contain an air detector.

In this way, the air bubbles possibly caused by the post-infusion remain separable with a line comprising a single air separator, without bringing about undesired coagulation in the extracorporeal circuit, in particular in the air separator.

The venous line 108 comprises a channel which can receive an occlusion means 114 downstream of the air detector. The occlusion means 114 comprises a clamp or a valve of another structure. In the event of air being detected, this means makes it possible to arrest the return of blood to the patient in order to eliminate the air bubbles detected.

The post-infusion line 112 is mounted immediately upstream of the air detector 113. Moreover the tube portion extending between the air detector and the connector to the patient is adapted not to receive any further injection device. The air detector operates as close as possible to the venous line connector 108 which is designed to receive a vascular access device 200 such as for instance a needle or a catheter. Indeed the air detector operates directly upstream the patient venous line conncetor 139.

Thus, the anticoagulant power of the pre-infusion solution is used through the greatest possible extent of the device.

The air separator 111 comprises a bubble trap. The solution for regional anticoagulation contains citrate ions, for example trisodium citrate dihydrate or a solution of Anticoagulant Citrate Dextrose (ACD), comprising trisodium citrate dihydrate and citric acid monohydrate.

The solution at least partially re-establishing the ionic equilibrium of the blood contains calcium ions. This solution can contain an isotonic solution comprising calcium chloride, potassium chloride and magnesium chloride.

Referring again to the sense of blood flow within the arterial line, the pre-infusion line 109 is connected to the arterial line upstream of any means 115 for regulating the flow rate of liquidin the arterial line 108.

According to one embodiment the pre-infusion line 109 is connected to the arterial line 106 as close as possible (immediately downstream of the patient arterial line connector 239 in reference to the patient blood flow) of the arterial line connector 239 to the patient which again is designed to receive a vascular access device 201 such as for instance a needle or a catheter.

In this way, the anticoagulation power of the pre-infusion solution is immediately available as soon as patient blood enters into the extracorporeal circuit.

The arterial line 106 is operationally associated with a first means 115 of regulating the flowrate of blood.

The pre-infusion line is operationally associated with a second means 119 of regulating the flowrate of liquid.

The post-infusion line 112 is operationally associated with a third means 121 of regulating the flowrate of liquid.

The purge line 110 issuing from the second chamber 104 of the filter 102 comprises a fourth means 123 of regulating the flowrate of liquid and a first means 124 of measuring the flowrate of liquid.

A calculation and control unit (CPU) 125 is able to receive the signals emitted by a first means 124 of measuring the flowrate operating on the purge channel 110 and for controlling one or more means 115, 119, 121, 123 of regulating the flowrate of liquid in order to initiate a haemofiltration operating mode.

The device for treating blood by extracorporeal circulation 101 comprises an intake line 126 to the second chamber 104 of the filter 102 connecting up with a source 127 of dialysis liquid, for example a container of sterilized liquid or a device for preparing liquid on line.

The citrate ions bind naturally to the calcium ions. This is why the dialysis liquid does not comprise calcium ions. This prevents reaction of the citrate contained in the pre-infusion with calcium which would be contained in the dialysis liquid. The citrate contained in the pre-infusion thus reacts solely with the calcium contained in the blood, and the anticoagulant power of the citrate is not attenuated by the dialysis liquid.

The intake line 126 comprises a fifth means 128 of regulating the flowrate of liquid and a second means 129 of measuring the flowrate of liquid.

A calculation and control unit (CPU) 125 is able to receive the signals emitted by one or more means 124, 129 of measuring the flowrate of liquid and for controlling one or more means 115, 119, 121, 123, 128 of regulating the flowrate of liquid in order to initiate a haemofiltration or haemodiafiltration operating mode.

Each means of regulating the flowrate of liquid 115, 119, 121, 123, 128 comprises a pump or a valve. Each means of measuring the flowrate of liquid 124, 129 comprises a flow meter.

A first balance 130 is provided for weighing a first reservoir 131 connected to the pre-infusion line 109 and containing the pre-infusion liquid; and a second balance 132 is provided for weighing a second reservoir 133 connected to the post-infusion line 112 and containing the post-infusion liquid.

The calculation and control unit 125 is able to receive the signals emitted by at least one of the two balances 130, 132. It controls one or more means 119, 121 of regulating the flowrate of liquid by periodically calculating the actual flowrate or a parameter which is a function of the actual flowrate.

Thus, the quantities of anticoagulant and of solution for re-establishing the ionic equilibrium can be known and controlled during the treatment. Knowing said weights, the calculation and control unit (125) is able to directly control the means of regulating the flowrate of liquid in order to obtain a desired quantity of pre-infusion solution and/or post-infusion solution in the extracorporeal circuit.

Figure 4:
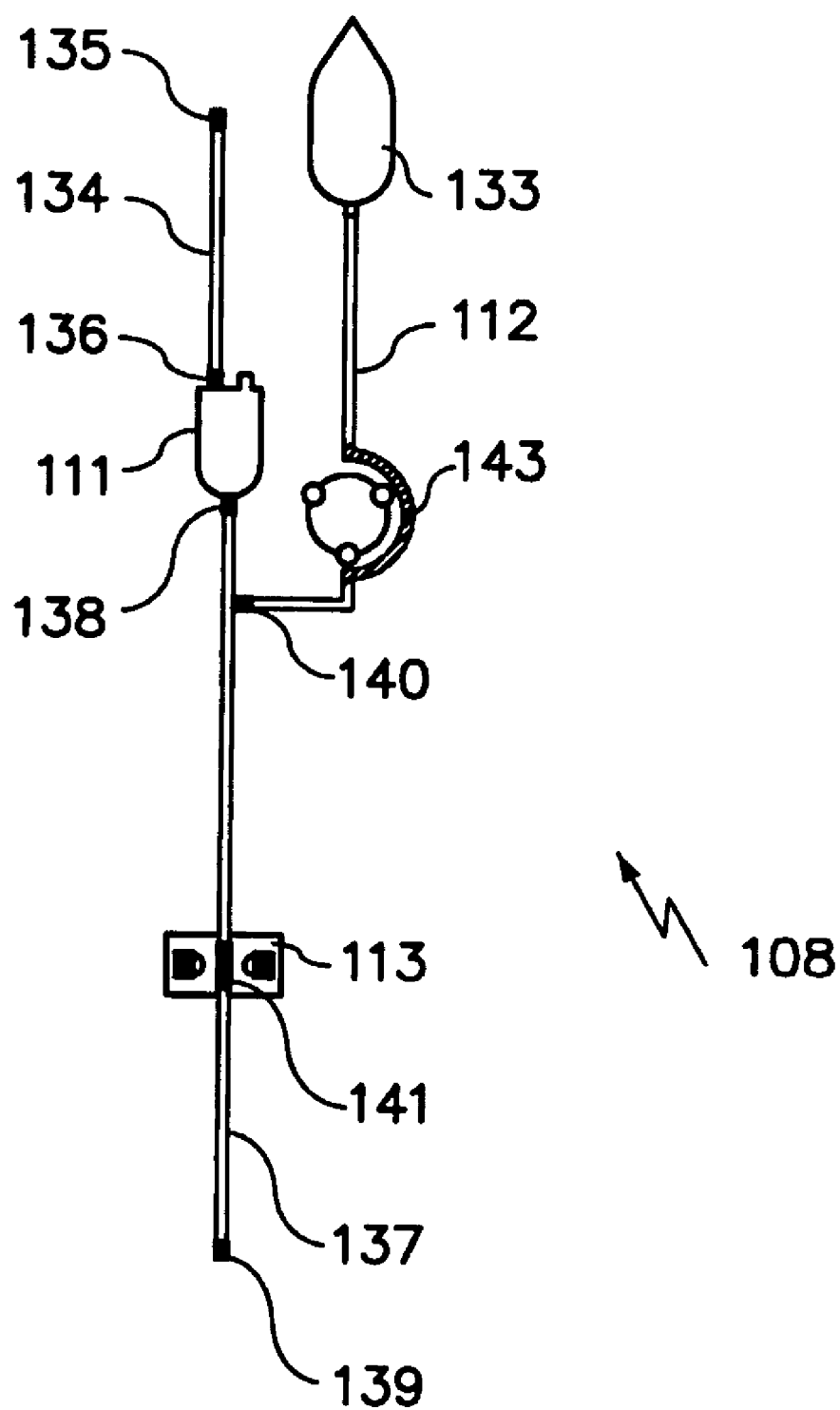
FIG. 4 shows a disposable line for treating blood by extracorporeal circulation according to the invention.

FIG. 4 shows the disposable venous line 108 for use in a circuit for extracorporeal circulation of blood having undergone pre-infusion of anticoagulant, said line comprising a first channel 134 having a first connector 135 for linking to a filter and a second connector 136. An air separator 111 is linked to the second connector 136 downstream of the first channel 134, that is to say downstream in the direction of the blood. The disposable venous line 108 also comprises a second channel 137 having a third connector 138 for linking the outlet of the air separator 111 and a fourth connector 139 for linking to the blood access of a patient. A fifth connector 140 is placed to connect a line 112 for post-infusion of a solution at least partially re-establishing the ionic equilibrium of the blood, the fifth connector 140 permitting fluid communication with the second channel 137. The line additionally comprises a first part 141 of the second channel 137 capable of cooperating with the air detector 113 and placed downstream of the fifth connector 140.

The first part 141 is marked visually, for example by different colours, a relief, by a tube differentiated in terms of material, shape or size from the rest of the line.

The post-infusion line 112 is linked to the second connector 140 in order to infuse the solution at least partially re-establishing the ionic equilibrium of the blood.

The fifth connector 140 will be connected on the second channel 137 as close as possible to the fourth connector 139.

The tube portion extending between the fifth connector 140 and the fourth connector 139 is continuous and adapted not to receive any further line or any further injection device.

The fifth connector 140 placed on the second channel 137 can be a removable connector. Alternatively, the connector 140 can comprise an end portion of the tube 112 fixed to the line 137.

No other air separator is inserted downstream of the first part 141 of the second channel 137 connectable to the air detector 113.

The air separator 111 can be the only air separator present in the disposable venous line 108.

The air separator 111 comprises a bubble trap.

The post-infusion line 112 comprises a second part 143 connectable to a means of regulating the flowrate of the perfusion line, said second part 143 being maintained in a U-shape by means of a small bar fixing two points of the line, in order to facilitate coupling with the pump.

The second part 143 is marked visually, for example by different colours, by a relief, by a tube differentiated in terms of material, shape or size from the rest of the line.

The first connector 135 of the first channel 134 is either removable or fixed.

The second connector 136 of the first channel 134 and the third connector 138 of the second channel 137 are fixed.

The fourth connector 139 of the second channel 137 is either fixed or removable.

The present invention affords numerous advantages. The air bubbles possibly introduced by the post-infusion remain detectable with a line comprising a single and unique bubble trap. The device thus has a simple and inexpensive structure.

Moreover, the use of said device, of said line and of said method does not entail undesired coagulation in the extracoporeal circuit, in particular in the bubble trap where the contact of air with the blood is possible and where the speed of displacement is less than in the rest of the venous line on account of the diameter of the bubble trap being larger than that of the rest of the line. This therefore results in effective prevention of administration of air to the patient.

Thus, the anticoagulant power of the pre-infusion solution is used throughout the greatest possible extent of the device because the pre-infusion of anticoagulant is injected as far as possible upstream in the extracorporeal circuit and the post-infusion of solution re-establishing ionic equilibrium is linked as close as possible to the blood access to the patient, that is to say as far downstream as is possible on the venous line. This link prevents coagulation throughout the portion of line where the need for anticoagulation arises, particularly where contact between the blood and air is possible. The configuration of the venous line is all the more advantageous since, as a result of the location of the site of administration of the neutralizing solution, the blood, no longer comprising anticoagulant substance, at no point can come into contact with the air.

In addition, the invention is very advantageous in cases where a device is operating for long periods, for example at a low blood flowrate in an intensive care unit, that is to say in acute treatment with a low flowrate and long duration.

It has been confirmed that the dialysis values measured during extracorporeal treatment according to the invention remain as stable as with an anticoagulant of the heparin type re-injected into the patient.

Thus, the result of anticoagulation is very advantageous because the coagulation time is increased fourfold between the perfusion of anticoagulant and the perfusion of neutralizing solution compared to the blood circulating in the rest of the circuit.

Finally, at the end of the session, the compression time needed for haemostasis of the fistula is reduced compared to treatment with administration of heparin because the blood re-injected into the patient has recovered its normal coagulating power.

The invention claimed is:

1. A device for treating blood by extracorporeal circulation comprising:
    a filter having a first chamber and a second chamber separated by a semi-permeable membrane;
    an arterial line connected to the first chamber of the filter;
    a venous line issuing from the first chamber of the filter, the venous line having a tube portion;
    a channel used for pre-infusion of a substance for local anticoagulation and linked to the arterial line;
    a purge channel issuing from the second chamber of the filter;
    an air separator on the venous line, said air separator being the only air separator present in the venous line and does not contain an air detector;
    a line for post-infusion of a solution at least partially re-establishing the ionic equilibrium of the blood downstream of the air separator;
    an air detector; and
    a reservoir connected to the post-infusion line and containing the solution at least partially re-establishing the ionic equilibrium of the blood, wherein, the post infusion line is mounted immediately upstream of the air detector, the tube portion of the venous line extending between the air detector and a patient venous line connector configured on said venous line, said tube portion being configured not to receive another line or another injection device.

2. A device for treating blood by extracorporeal circulation according to claim 1, wherein the venous line comprises a channel configured to receive an occlusion means downstream of the air detector.

3. A device for treating blood by extracorporeal circulation according to claim 2, wherein the occlusion means is a clamp.

4. A device for treating blood by extracorporeal circulation according to claim 1, wherein the air separator comprises a bubble trap.

5. A device for treating blood by extracorporeal circulation according to claim 1, wherein the solution for regional anticoagulation contains citrate ions.

6. A device for treating blood by extracorporeal circulation according to claim 5, wherein the solution for regional anticoagulation contains a solution of trisodium citrate dihydrate.

7. A device for treating blood by extracorporeal circulation according to claim 5, wherein the solution for regional anticoagulation contains a solution of Anticoagulant Citrate Dextrose (ACD) comprising trisodium citrate dihydrate and citric acid monohydrate.

8. A device for treating blood by extracorporeal circulation according to claim 1, wherein the solution at least partially re-establishing the ionic equilibrium of the blood contains calcium ions.

9. A device for treating blood by extracorporeal circulation according to claim 8, wherein the solution at least partially re-establishing the ionic equilibrium of the blood contains an isotonic solution comprising calcium chloride, potassium chloride, and magnesium chloride.

10. A device for treating blood by extracorporeal circulation according to claim 1, wherein the channel used for pre-infusion is connected immediately downstream of a patient arterial line connector.

11. A device for treating blood by extracorporeal circulation according to claim 1 comprising means for regulating the blood flow rate, the channel used for pre-infusion being connected to the arterial line upstream said regulating means.

12. A device for treating blood by extracorporeal circulation according claim 11, wherein said regulating means comprises first means for regulating the blood flow rate associated with the arterial line.

13. A device for treating blood by extracorporeal circulation according to claim 12, wherein said regulating means comprises second means for regulating the flow rate of liquid operationally associated with the channel used for pre-infusion.

14. A device for treating blood by extracorporeal circulation according to claim 13, wherein said regulating means comprises third means for regulating the flow rate of liquid operationally associated with the post-infusion line.

15. A device for treating blood by extracorporeal circulation according to claim 14, wherein said regulating means comprises fourth means for regulating the flow rate of liquid operationally associated with the purge channel issuing from the second chamber of the filter.

16. A device for treating blood by extracorporeal circulation according to claim 15, comprising a second means for measuring the flowrate of liquid operating on the intake line and fifth means for regulating the flowrate of liquid operating on the intake line.

17. A device for treating blood by extracorporeal circulation according to claim 16, wherein the calculation and control unit receives the signals emitted by one or more means for measuring the flowrate of liquid and controls one or more means for regulating the flowrate of liquid in order to initiate a hemofiltration or hemodiafiltration operating mode.

18. A device for treating blood by extracorporeal circulation according to claim 11 comprising first means for measuring the flow rate of liquid operating on the purge channel and comprising a calculation and control unit for receiving the signals emitted by said measuring means and for controlling one or more means for regulating the flow rate.

19. A device for treating blood by extracorporeal circulation according to claim 11, comprising an intake line to the second chamber of the filter connecting up with a source of dialysis liquid.

20. A device for treating blood by extracorporeal circulation according to claim 19, wherein the dialysis liquid does not comprise calcium ions.

21. A device for treating blood by extracorporeal circulation according to one of claims 18, 19, 20 or 16 wherein the means of measuring the flowrate of liquid comprises a flow meter.

22. A device for treating blood by extracorporeal circulation according to claim 11, wherein each means of regulating the flowrate of liquid comprises a pump or a valve.

23. A device for treating blood by extracorporeal circulation according to claim 1, comprising a first balance for weighing a first reservoir connected to the channel used for pre-infusion and containing the substance for local anticoagulation.

24. A device for treating blood by extracorporeal circulation according to claim 23, comprising a second balance for weighing a second reservoir connected to the post-infusion line and containing the solution at least partially re-establishing the ionic equilibrium of the blood.

25. A device for treating blood by extracorporeal circulation according to claim 1, comprising:
    means for regulating the blood flow rate, the channel used for pre-infusion being connected to the arterial line upstream said regulating means;
    a first balance for weighing a first reservoir connected to the channel used for pre-infusion and containing the substance for local anticoagulation;
    a second balance for weighing a second reservoir connected to the post-infusion line and containing the solution at least partially re-establishing the ionic equilibrium of the blood; and
    a calculation and control unit for receiving the signals emitted by at least one of the two balances and for controlling one or more means of regulating the flowrate of liquid.

* * * * *

UNITED STATES PATENT AND TRADEMARK OFFICE
CERTIFICATE OF CORRECTION

PATENT NO. : 7,351,218 B2  Page 1 of 1
APPLICATION NO. : 10/739273
DATED : April 1, 2008
INVENTOR(S) : Bernard Bene It is certified that error appears in the above-identified patent and that said Letters Patent is hereby corrected as shown below:

In claim 12, column 9, line 38, "according claim" should read --according to claim--.

Signed and Sealed this

Fifth Day of August, 2008

JON W. DUDAS
*Director of the United States Patent and Trademark Office*